United States Patent [19]
Southard et al.

[11] Patent Number: 5,962,006
[45] Date of Patent: Oct. 5, 1999

[54] POLYMER FORMULATION FOR PREVENTION OF SURGICAL ADHESIONS

[75] Inventors: Jeffrey L. Southard, Aurora; Richard L. Dunn, Fort Collings, both of Colo.

[73] Assignee: Atrix Laboratories, Inc., Fort Collins, Colo.

[21] Appl. No.: 08/877,391

[22] Filed: Jun. 17, 1997

[51] Int. Cl.$^6$ ............................. A61K 9/08; A61K 47/34; A61K 47/22
[52] U.S. Cl. ............................................. 424/426; 424/400
[58] Field of Search ...................................... 424/400, 423, 424/426, 428, 78.38, 486; 514/772.7

[56] References Cited

U.S. PATENT DOCUMENTS

| | | |
|---|---|---|
| 3,218,283 | 12/1965 | Miller . |
| 4,148,871 | 4/1979 | Pitt et al. . |
| 4,186,190 | 1/1980 | Gregory . |
| 4,293,539 | 10/1981 | Ludwig et al. . |
| 4,379,914 | 4/1983 | Lundberg . |
| 4,492,685 | 1/1985 | Keith et al. . |
| 4,542,012 | 9/1985 | Dell . |
| 4,579,731 | 4/1986 | Fox, Jr. et al. . |
| 4,595,713 | 6/1986 | St. John . |
| 4,605,730 | 8/1986 | Shalaby et al. . |
| 4,624,256 | 11/1986 | Messier et al. . |
| 4,818,542 | 4/1989 | DeLuca et al. . |
| 4,913,903 | 4/1990 | Sudmann et al. . |

(List continued on next page.)

FOREIGN PATENT DOCUMENTS

| | | |
|---|---|---|
| 0 159 293 A1 | 10/1985 | European Pat. Off. . |
| 0 271 831 A2 | 6/1988 | European Pat. Off. . |
| 0 297 535 A3 | 1/1989 | European Pat. Off. . |
| 0 430 474 B1 | 6/1991 | European Pat. Off. . |
| 0 484 387 B1 | 5/1992 | European Pat. Off. . |
| 0 521 455 A2 | 1/1993 | European Pat. Off. . |
| 2 017 113 | 10/1979 | United Kingdom . |
| 2 223 027 | 3/1990 | United Kingdom . |

OTHER PUBLICATIONS

Blanchard, P., "Technology of Corn Wet Milling", *Industrial Chemistry Library*, 4:142–143 (1992).
*Encyclopedia of Chemical Technology* 4th Ed. (1997), John Wiley & Sons, Inc., 22:699–719.
Fuchs, O., "Solvents and Non–Solvents for Polymers", *Polymer Handbook*, 3rd Ed., pp. 379–380, 104 (1989).
*Hawley's Condensed Chemical Dictionary*, 11th Ed. (1987), Van Nostrand Reinhold Company, New York, pp. 1098–1090, 1146.
Whistler, *Starch: Chemistry and Technology*, 2nd Ed. (1984), Academic Press, Inc., New York, pp. 232–233.
Dunn et al., "An Injectable Implant Delivery System for Antimicrobial Agents", *Polymer Preprints*, 31(2) 189–191 (Aug., 1990).
*Treatise on Controlled Drug Delivery, Fundamentals, Optimization, Application*, Ed by Agis Kydonieus, Marcel Dekker, Ionc., p. 203.

*Primary Examiner*—Edward J. Webman
*Attorney, Agent, or Firm*—Merchant & Gould P.C.

[57] ABSTRACT

The invention is directed to a polymer formulation in which a pharmaceutically acceptable, biocompatible, biodegradable and/or bioerodible, water-coagulable thermoplastic polymer or copolymer which is substantially insoluble in an aqueous medium is dissolved in $\epsilon$-caprolactone, a pharmaceutically-acceptable, moderately water-soluble organic solvent. When brought in contact with an aqueous environment, such as body or tissue fluids, the $\epsilon$-caprolactone slowly dissipates into the aqueous fluid. As the $\epsilon$-caprolactone dissipates, the water-insoluble thermoplastic polymer coagulates to form a flexible matrix. Preferably, the thermoplastic polymer is a copolymer of caprolactone or methylene carbonate and lactide or glycolide monomers. More preferably, the thermoplastic polymer is poly(DL-lactide-co-caprolactone). The polymer formulation may also contain a biologically active agent and/or a rate modifying agents to control the rate of release of the biologically active agent. The invention is also directed to a method of making the pliable matrix and the pliable matrix itself.

7 Claims, 4 Drawing Sheets

U.S. PATENT DOCUMENTS

| | | |
|---|---|---|
| 4,921,691 | 5/1990 | Stockel . |
| 4,938,763 | 7/1990 | Dunn et al. . |
| 4,975,271 | 12/1990 | Dunn et al. . |
| 5,077,049 | 12/1991 | Dunn et al. . |
| 5,133,981 | 7/1992 | Harkrader et al. . |
| 5,278,201 | 1/1994 | Dunn et al. . |
| 5,278,202 | 1/1994 | Dunn et al. . |
| 5,324,519 | 6/1994 | Dunn et al. . |
| 5,324,520 | 6/1994 | Dunn et al. . |
| 5,340,849 | 8/1994 | Dunn et al. . |
| 5,368,859 | 11/1994 | Dunn et al. . |
| 5,487,897 | 1/1996 | Polson et al. . |
| 5,609,855 | 3/1997 | Oh et al. . |
| 5,632,727 | 5/1997 | Tipton et al. . |
| 5,660,849 | 8/1997 | Polson et al. . |
| 5,681,873 | 10/1997 | Norton et al. . |

POLYMER FORMULATION FOR PREVENTION OF SURGICAL ADHESIONS

BACKGROUND OF THE INVENTION

Adhesions are fibrous bands of tissue connecting one or more organ sites within the body. Typically, adhesions are formed in connection with tissue injury. Injury to, or ischemia of, serosal tissue results in an increased immune response at the site, with a subsequent release of serosanguinous exudate resulting in fibrin deposition at the injured site. Adhesions form as a result of the induced inflammatory response in combination with an impaired ability to lyse such fibrin deposits.

Normal tissue surfaces produce tissue plasminogen activator (t-PA) which converts inactive plasminogen to plasmin. In normal tissue, the localized proteolytic activity of plasmin dissolves fibrin deposits and thus prevents adhesion formation. However, ischemic injury to serosal surfaces retards t-PA production. Reduced t-PA production results in excessive fibrin accumulation at the injured site. Such fibrin deposits serve as a matrix for fibroblastic infiltration and proliferation. Eventually, collagenous bands form at the site of the fibrin deposit. The collagenous bands contract as healing proceeds and thereby limit movement of the affected organ or organs.

Consequently, adhesions impair movement and can obstruct proper organ function. Such mechanical impairment is responsible for a majority of chest, back, abdominal, and pelvic pain experienced by patients recovering from thoracic, abdominal, lumbar and/or gynecological surgeries. Additionally, adhesions may complicate proper healing of the surgical site and lead to loss of function, infertility, bowel obstruction and even morbidity.

Two different strategies have been employed to prevent the formation of fibrous adhesions following surgery. A first strategy includes the use of barrier materials such as oxidized cellulose membranes, polytetrafluoroethylene, or hyaluronic acid. These barrier materials are typically applied as films or sheets and sutured in place to prevent the deposition of fibrin on the injured tissue.

However, oxidized cellulose membranes, such as the Interceed™ Barrier are difficult to place and require a nonbleeding site. Films such as Gore-Tex™ have to be sutured in place. Other membranes, such as Seprafilm™ hyaluronic acid films, are brittle and frequently crack during application. Because a cracked film does not isolate the injured tissue from surrounding tissue, adhesion formation is not satisfactorily prevented. Such films also stick to moist gloves, other tissues and instruments thus interfering with their application. Additionally, once such films are applied to a tissue, the positioning of the film cannot be altered. Therefore, medical personnel do not have an opportunity to optimize the positioning of the film once it is applied to a tissue defect. Finally, many films, such as Gore-Tex™, are not biodegradable and must eventually be removed. The removal process may cause additional trauma or injury to the tissue.

Other barrier materials include viscous liquids, such as hyaluronic acid solutions, which are applied to a surgical site. However, the viscous liquid frequently does not coat the surgical site for a sufficient duration to provide the necessary barrier properties. Aqueous solutions of poloxamers, such as pluronics, which are liquids at or below room temperature, but form gels at body temperature have been developed for preventing surgical adhesions.

Although a number of these barrier materials have been approved for use in humans by the FDA, their widespread use has been limited because of their difficulty in placement and their perceived efficacy.

A second strategy for preventing adhesion formation involves the use of pharmacological agents. Typical pharmacological agents include corticosteroids and nonsteroidal anti-inflammatory agents (to inhibit fibroblastic proliferation); heparin and sodium citrate (to prevent fibrin deposition); and pentoxifylline, rt-PA, urokinase and streptokinase (to promote fibrinolysis). Unfortunately, the success of pharmacological agents in preventing adhesion formation has been limited, due to the difficulty of directing the drugs to the injury with systemic administration.

It would therefore be desirable to have a system for preventing adhesion formation which is more "user friendly" and more effective than the existing barrier materials. In particular, a barrier material that does not stick to instruments during application and is adjustable after initial application would be desirable. Additionally, a system for local administration of pharmacological agents which prevent adhesion formation would be desirable.

SUMMARY OF THE INVENTION

The invention is directed to a polymer formulation in which a pharmaceutically acceptable, biocompatible, biodegradable and/or bioerodible, water-coagulable thermoplastic polymer or copolymer which is substantially insoluble in an aqueous medium is dissolved in $\epsilon$-caprolactone, a pharmaceutically-acceptable, moderately water-soluble organic solvent. When brought in contact with an aqueous environment, such as body or tissue fluids which typically surround tissues or organs in an organism, $\epsilon$-caprolactone slowly dissipates into the aqueous or body fluid. As $\epsilon$-caprolactone dissipates, the water-insoluble thermoplastic polymer coagulates to form a flexible matrix or film. Preferably, the thermoplastic polymer is a copolymer of caprolactone or trimethylene carbonate monomers and lactide or glycolide monomers. More preferably, the thermoplastic polymer is poly(DL-lactide-co-caprolactone).

The concentration of the polymer in the $\epsilon$-caprolactone can be adjusted to alter the consistency of the formulation, from a low-viscosity, water-like substance to a high viscosity, paste-like material. The polymer formulation can be applied to a patient's tissues in any convenient manner. However, it is preferred that the formulation have a consistency wherein it can be sprayed onto tissue using an air brush, thereby forming a uniform, thin protective film. Another example of an alternative method of application includes dripping the formulation onto a tissue. A biologically active agent can also be added to the polymer formulation to provide local delivery of the agent at the surgical site. The biologically active material can include any biologically, physiologically, or pharmacologically active substance that acts locally or systemically in a human or animal body. Exemplary biologically active materials include anti-inflammatory agents, antibiotics, analgesics, anesthetics, antiseptics, and agents which prevent fibrin deposition or enhance fibrinolysis.

Rate modifying agents can be used to control the rate of release of the biologically active material. Examples of suitable release rate modification agents include dimethyl citrate, triethyl citrate, ethyl heptanoate, glycerin, and hexanediol.

The invention is also directed to a method of making the pliable matrix and the pliable matrix itself.

The formation of a solid, but flexible, matrix in-situ appears to eliminate many of the application problems associated with preformed barrier materials. Because the polymer formulation of the invention forms a pliable matrix in-situ, the matrix does not adhere to instruments or the gloves of medical personnel during application. Because the formulation slowly coagulates to form a solid, flexible matrix, placement of the flowable formulation on the tissue defect can be optimized after the polymer formulation is applied. Additionally, the formulation conforms to a patient's tissue, even as the tissues are manipulated by medical personnel. Therefore, the resulting matrix does not pull away from the tissue or crack when the patient's organs or tissues are manipulated. This is particularly beneficial where an organ is being placed in a body cavity after the polymer formulation is applied, for example, near the end of a surgical procedure. Other benefits of the polymer formulation of the invention include its ability to be applied laproscopically to a surgical site due to its flowable form.

DETAILED DESCRIPTION OF THE INVENTION

The invention is directed to a polymer formulation for preventing formation of adhesions, particularly after cardiac, thoracic, abdominal, pelvic or gynecological surgery. The polymer formulation includes a pharmaceutically acceptable, biodegradable thermoplastic polymer that is substantially insoluble in water or human or animal body fluids. The thermoplastic polymer is dissolved in $\epsilon$-caprolactone, a biocompatible organic solvent which is moderately soluble in water or human or animal body fluids. According to the invention, $\epsilon$-caprolactone dissipates slowly into surrounding tissue fluids when the polymer formulation is applied to a tissue defect. As the $\epsilon$-caprolactone dissipates, the water-insoluble thermoplastic polymer slowly coagulates to form a pliable matrix. Preferably, the thermoplastic polymer is a copolymer of caprolactone or trimethylene carbonate monomers and lactide or glycolide monomers. More preferably, the thermoplastic polymer is poly(DL-lactide-co-caprolactone).

The resulting matrix provides a flexible, biodegradable barrier which prevents formation of tissue adhesions between the tissue defect and neighboring tissues. Because the resulting matrix is biodegradable, bioabsorbable, and/or bioerodible, it is gradually absorbed into surrounding tissue fluids, for example, blood serum, lymph, cerebral spinal fluid (CSF), or periodontal fluid and/or becomes disintegrated through enzymatic, chemical or cellular hydrolytic action. The amount of time required to degrade the matrix can be varied, for example, by altering the molecular weight of the thermoplastic polymer or the composition of the copolymer. Generally, the matrix is absorbed over a period of about 1 week to about 12 months, preferably within about 1 week to about 2 weeks.

Although systems in which thermoplastic polymers are dissolved in a biocompatible, water soluble organic solvent and form a solid implant upon contact with body fluids have been described (See, for example, Dunn et al., U.S. Pat. No. 5,324,519), the inventors have found, surprisingly, that dissolving a thermoplastic polymer, such as poly(DL-lactide-co-caprolactone), in $\epsilon$-caprolactone results in an in-situ barrier film that is more effective at preventing adhesion formation than formulations prepared with other solvents. While not intending to be bound by theory, the inventors believe that the surprising efficacy is due either to the slow coagulation of the elastomeric copolymer (due to the moderate solubility of $\epsilon$-caprolactone in aqueous media) or the inherent properties of the caprolactone solvent. Additionally, the thermoplastic polymer used in the formulation may impact the efficacy of the formulation. Preferably, the thermoplastic polymer or copolymer is elastomeric such that the resulting matrix is pliable and able to conform to the underlying tissue, even when the tissue is moved, for example when the tissue is manipulated by medical personnel.

Definitions

As used herein, the term "tissue defect" includes any injured tissue, such as abraded tissue, traumatized tissue, a surgical incision or surgically resected tissue. Examples of tissue defects include, but are not limited to, surgical incisions in an internal organ such as an ovary, heart, liver, intestine, stomach, etc . . . . A tissue defect is typically surrounded by an aqueous or body fluid such as interstitial fluid, blood, serum, cerebrospinal fluid or peritoneal fluid.

The term "biodegradable" means that the polymer and/or polymer matrix of the film will degrade over time by the action of enzymes, by hydrolytic action and/or by other similar mechanisms in the human body. By "bioerodible," it is meant that the film matrix will erode or degrade over time due, at least in part, to contact with substances found in the surrounding tissue fluids or cellular action. By "bioabsorbable," it is meant that the polymer matrix will be broken down and absorbed within the human body, for example, by a cell or tissue. "Biocompatible" means that neither the polymer, the solvent nor the resulting film cause substantial tissue irritation or necrosis at the tissue defect.

"Flowable" means that the polymer formulation is easy to manipulate and may be shaped and molded within the tissue defect as it coagulates. Flowable includes formulations with a low viscosity or water-like consistency to those with a high viscosity, such as a paste-like material. Advantageously, the flowability of the polymer formulation allows it to conform to irregularities, crevices, cracks, and/or holes in the tissue defect.

As used in connection with the invention, an organic solvent that is "moderately" soluble in an aqueous medium will dissipate slowly in the aqueous medium. Thus, the thermoplastic polymer slowly precipitates or coagulates to form a flexible matrix. As used herein, "slowly" means that medical personnel have time to manipulate the polymer formulation after it has been applied to a patient's tissue but before the solvent dissipates and the thermoplastic polymer precipitates to form a flexible matrix. The lingering flowable polymer formulation can adapt to a tissue's contours as the organ or tissue is manipulated during surgery, particularly as the organ is placed in the appropriate body cavity near the end of the surgical procedure. Typically, "slowly" means that the polymer matrix takes about 5 minutes to about 30 minutes to form, more preferably takes about 5 minutes to about 10 minutes to form. Typically, a "moderately" water soluble organic solvent has a water solubility of about 5% to about 25% weight percent.

"Substantially insoluble" in an aqueous medium means that the thermoplastic polymer does not dissolve in an aqueous medium.

"Soluble" in an organic solvent means that the thermoplastic polymer dissolves at a concentration of about 10% to about 70% by weight in an organic solvent.

As used herein, a "pliable" or "flexible" matrix is able to conform to a patient's tissue and allow the underlying tissue to move without restraint or without the polymer matrix pulling away from the underlying tissue.

Thermoplastic Polymers

Thermoplastic polymers useful in the polymer formulation include pharmaceutically acceptable polymers that are biodegradable, bioabsorbable, and/or bioerodible. The thermoplastic polymers are capable of substantially dissolving in a water-soluble carrier, or solvent, to form a solution. According to the invention, the thermoplastic polymers are elastomeric so that the resulting film is flexible or pliable. Typically, the thermoplastic polymer is a copolymer with a flexible, amorphous segment, such as polycaprolactone, coupled to a more rigid segment, such as glycolide or lactide. Thermoplastic polymers that are suitable for use in the polymer formulation generally include any having the foregoing characteristics. Examples of suitable thermoplastic polymers include copolymers of caprolactone or trimethylene carbonate monomers and lactide or glycolide monomers. Because poly(DL-lactide-co-caprolactone) provides a matrix which is the most flexible and adherent to tissue, most preferably, the thermoplastic polymer is poly(DL-lactide-co-caprolactone).

The ratio of monomers in the copolymer can affect the strength and flexibility of the film. For example, a copolymer having a high lactide or glycolide content will tend to be rigid. A copolymer having a high caprolactone content tends to crystallize, and is therefore also rigid. It is preferred that the copolymer have a suitable amount of caprolactone or trimethylene carbonate monomers combined with a suitable amount of lactide or glycolide monomers such that the thermoplastic polymer is flexible and the resulting matrix is able to conform to the surface of the underlying tissue, even when the underlying tissue is manipulated or moved. An example of a suitable copolymer includes a thermoplastic polymer containing about 10%–90% lactide and 90%–10% caprolactone; more preferably, containing 25%–75% lactide and 75%–25% caprolactone. Most preferably, the thermoplastic polymer contains 35–75% lactide and 65–25% caprolactone.

The inherent viscosity (abbreviated as "I.V."; units are in deciliters/gram) of the thermoplastic polymer is a measure of its molecular weight and degradation time (e.g., a thermoplastic polymer with a high inherent viscosity has a longer degradation time). Although a thermoplastic polymer with a high molecular weight provides a stronger matrix, the matrix takes more time to degrade. In contrast, a thermoplastic polymer with a low molecular weight degrades more quickly, although the matrix may be too soft. To produce a film with a desired strength and degradation time, typically, the inherent viscosity of the thermoplastic polymer should be from about 0.25 dL/g to about 1.5 dL/g (as measured in chloroform), more preferably from about 0.50 dL/g to about 0.90 dL/g.

The molecular weight of the thermoplastic polymer can be varied by many methods known in the art. The choice of method is typically determined by the type of polymer. For example, the degree of polymerization can be controlled by varying the amount of initiator and/or reaction time.

Polymer Formulation

According to the invention, the thermoplastic polymer is combined with $\epsilon$-caprolactone, an organic solvent, to form a polymer formulation. According to the invention, the thermoplastic polymer is soluble in $\epsilon$-caprolactone and the $\epsilon$-caprolactone is moderately soluble in an aqueous medium, such that, upon contact with an aqueous medium, the $\epsilon$-caprolactone slowly diffuses from the polymer formulation into the aqueous medium and the thermoplastic polymer slowly precipitates or coagulates to form a pliable matrix.

Preferably the "primary" biocompatible organic solvent is $\epsilon$-caprolactone. As used in connection with the invention, a "primary" solvent is present in a major amount (e.g., greater than about 50% by weight). In addition to having the properties described above, experimental results indicate that polymer formulations having $\epsilon$-caprolactone as a solvent results in a greater reduction in adhesion formation than formulations prepared with other organic solvents. While not intending to be bound by theory, it is believed that a polymer formulation with $\epsilon$-caprolactone as a solvent is particularly effective at reducing adhesion formation due to the slow dissipation of caprolactone into the aqueous environment. Alternatively, the efficacy of $\epsilon$-caprolactone may be due to the extended exposure of the tissue defect to a chemical or inherent property of $\epsilon$-caprolactone, because $\epsilon$-caprolactone dissipates slowly into the aqueous environment.

The concentration of thermoplastic polymer in the polymer formulation may affect the rate at which the formulation coagulates to form a matrix (e.g., a polymer formulation with a higher concentration of thermoplastic polymer may coagulate more quickly to form a film). As discussed above, it is preferable to have a polymer formulation which coagulates slowly. The percentage of polymer present in the formulation may also affect formulation viscosity. For example, a formulation having a higher percentage by weight of polymer is typically thicker and more viscous than a formulation having a lower percentage by weight of polymer. A more viscous formulation tends to flow more slowly. Therefore, a formulation having a lower viscosity may be preferred in some instances, for example, when applying the formulation via an aerosol spray. To achieve a slow coagulation rate, the polymer formulation preferably includes about 15 to about 40% by weight of the thermoplastic polymer, more preferably about 15 to about 25% by weight of the thermoplastic polymer.

Secondary Solvents

Although the thermoplastic polymer is preferably combined with $\epsilon$-caprolactone as a "primary" solvent, other solvents ("secondary" solvents) may be present in minor amounts. Preferably, secondary solvents are present in the polymer formulation an amount less than 50% by weight, more preferably less than 25% by weight.

A mixture of solvents may be used to provide varying degrees of solubility for the thermoplastic polymer or to alter the coagulation rate of a polymer formulation. Suitable secondary solvents include biocompatible, pharmaceutically-acceptable, solvents that are miscible with the thermoplastic polymer and capable of diffusing into an aqueous medium (i.e., tissue fluids, such as blood, serum, lymph, cerebral spinal fluid (CSF), and peritoneal fluid). Suitable secondary solvents include, for example, N-methyl-2-pyrrolidone, 2-pyrrolidone, $C_2$ to $C_6$ alkanols, propylene glycol, acetone, alkyl esters such as methyl acetate, ethyl acetate, ethyl lactate, alkyl ketones such as methyl ethyl ketone, dialkylamides such as dimethylformamide, dimethylacetamide, dimethyl sulfoxide, dimethyl sulfone, diethyl malonate, tetrahydrofuran, cyclic alkyl amides such as caprolactam and propylene carbonate.

Formation of a Polymer Matrix

In general, a solid, flexible matrix is formed by dispensing the flowable polymer formulation onto the surface of a tissue which is surrounded by an aqueous medium. The formulation can be applied to a patient's tissues by any convenient technique. For example, the formulation can be applied by brushing, spraying, extruding, dripping, injecting, or painting. Spraying, via aerosolization is a preferred method of administration because it minimizes the amount of formulation applied to the tissue defect while maximizing uniformity. A thin, uniform matrix, such as that formed by spraying, can also be called a film. Typically, the film has a thickness of about 10 $\mu$m to about 100 $\mu$m, more preferably from about 20 $\mu$m to about 50 $\mu$m. Spraying is a preferred method for applying the polymer formulation to a large surface area, such as peritoneal sidewalls. In contrast, dripping may be preferred for applying the polymer formulation to a small surface area, such as a bowel resection.

Optionally, after the polymer formulation is applied to a tissue defect, an aqueous solution, such as a saline solution, can be applied over the polymer formulation to enhance coagulation of the thermoplastic polymer to form the matrix.

Use of the Polymer Formulation

The polymer formulation can be used to prevent the formation of adhesions between a tissue defect, such as an abrasion or surgical incision, and neighboring tissues. According to the invention, a flowable polymer formulation is applied to a tissue defect in an animal. Once in contact with the aqueous environment surrounding the tissue defect, the $\epsilon$-caprolactone solvent slowly dissipates from the polymer formulation and the thermoplastic polymer slowly coagulates or precipitates to form a pliable matrix or film. Because the matrix forms slowly, the lingering flowable polymer formulation is able to conform to the surface of the tissue as it is manipulated by medical personnel (typically while placing the organ into the appropriate body cavity at the end of a surgical procedure). Consequently, the matrix does not crack or peel off the tissue shortly after application. Additionally, the slow coagulation of the matrix results in a formulation that does not adhere to the gloves of the medical personnel or instruments. Once the organ is in place, the polymer formulation coagulates to form a flexible matrix.

In contrast to a formulation which includes a slowly dissipating solvent as a primary solvent, application of a formulation which has a "rapidly" dissipating solvent as the primary solvent to a tissue defect in an aqueous environment results in the rapid precipitation of the thermoplastic polymer to form a matrix. When the matrix or film forms before medical personnel have completed manipulating the tissue (e.g., "rapidly"), the resulting matrix or film, which is not flowable like the polymer formulation, frequently pulls away from the tissue or cracks as the tissues are manipulated. Consequently, a rapidly forming matrix does not form a suitable barrier to prevent adhesion formation. Additionally, a rapidly dissipating solvent typically results in a film that adheres to the gloves of medical personnel when manipulating the film. A rapidly forming film also tends to adhere to instruments used during the surgical procedure. Examples of rapidly dissipating solvents include N-methyl-2-pyrrolidone and dimethyl sulfoxide.

It should be noted that a "rapidly" dissipating solvent may be included in the polymer formulation of the invention as a secondary solvent, for example, to alter the coagulation rate of the formulation.

The Polymer Matrix

When the polymer formulation is applied to a tissue defect, the organic solvent slowly dissipates into the surrounding aqueous or body fluids and the water-insoluble thermoplastic polymer precipitates or coagulates to form a polymer matrix. According to the invention, the resulting matrix is pliable and solid and able to conform with the irregular surface of the tissue, even when the tissue is moved. Because the thermoplastic polymers used in the formulation are elastomeric, the resulting matrix is very flexible and therefore does not restrict movement of the underlying tissues. This results in less pain experienced by a patient during the healing process.

Biologically-Active Agent

Optionally, the polymer formulation may include a biologically-active agent, such that the resulting matrix provides a delivery system for the agent to adjacent or distant tissues and organs in the animal. Biologically-active agents which may be used alone or in combination in the polymer system include medicaments, drugs, or other suitable biologically-, physiologically-, or pharmaceutically-active substances capable of providing a local or systemic biological, physiological or therapeutic effect and of being released from the resulting matrix into adjacent or surrounding tissue fluids.

The biologically-active agent may be soluble in the polymer formulation, to form a homogeneous mixture, or insoluble in the polymer formulation to form a suspension or dispersion. As the polymer formulation coagulates to form a matrix, the biologically-active agent preferably becomes incorporated into the matrix. As the matrix degrades over time, the biologically-active agent is released into adjacent tissue fluids, preferably at a controlled rate. The release of the biologically-active agent from the matrix may be varied, for example, by the solubility of the biologically-active agent in an aqueous medium, the distribution of the agent within the matrix and the size, shape, porosity, solubility or biodegradability of the matrix.

Preferably, the polymer formulation includes the biologically-active agent in an amount effective to provide the desired level of biological, physiological, pharmacological and/or therapeutic effect in the animal. There is generally no critical upper limit on the amount of the bioactive agent included in the polymer formulation. However, the bioactive agent should not be present in such a high concentration that the bioactive agent significantly alters the viscosity of the formulation and interferes with its application to a patient's tissues. The lower limit of the amount of bioactive agent incorporated into the polymer formulation depends on the activity of the bioactive material and the period of time desired for treatment. Generally, the concentration of a bioactive agent in the polymer formulation is about 0.01–400 mg per gram of polymer formulation.

The biologically-active agent may stimulate a biological or physiological activity with the animal. For example, the biologically active agent may be a substance useful in preventing infection at the tissue defect such as an antibacterial agent such as a penicillin, tetracycline cephalosporin, or bacitracin. Alternatively, the biologically active agent may be a substance useful in preventing the deposition of fibrin or enhancing fibrinolysis. Examples of such biologically active agents include heparin, sodium citrate, pentoxifylline, tissue plasminogen activator (rt-PA), urokinase, streptokinase, aprotinin (Aprot), and $\epsilon$-amino-n-caproic acid ($\epsilon$AnC). Suitable biologically-active agents for use in the invention also include anti-inflammatory agents such as corticosteroids like hydrocortisone or prednisone; or nonsteroidal anti-inflammatory agents such as flurbiprofen or ibuprofen.

Preferred biologically active agents include anti-inflammatory agents, agents which prevent fibrin deposition, agents which enhance fibrinolysis, and antibacterial agents.

Release Rate Modification Agents

The polymer formulation may include a release rate modification agent to provide controlled, sustained release of a bioactive agent from the matrix. Although not intended to be a limitation to the present disclosure, it is believed the release rate modification agent alters the release rate of a bioactive agent from the matrix by changing the hydrophobicity of the matrix.

For other examples and further discussion of release rate modification agents, or rate modifying agents, for use in the present invention, see Applicants' corresponding U.S. patent application Ser. No. 07/776,816, filed Oct. 15, 1991, the disclosure of which is incorporated by reference herein.

Other Means to Modify Release of Biologically Active Agent

The release rate of the bioactive agent from the matrix may also be adjusted by varying the concentration of the polymer in the polymer formulation. For example, the more dilute the polymer concentration, the more readily the bioactive agent will be released from the matrix. This can be used in combination with other means to more effectively control the release of the bioactive agent from the matrix. For example, by adjusting the concentration of the polymer and/or the bioactive agent, together with altering the molecular weight of the polymer and/or the amount of release rate modification agent, a wide range of release rates can be achieved.

For other examples and further discussion of controlling the rate of release of a bioactive agent from a matrix by varying the composition of the polymer formulation, see Applicants' corresponding U.S. patent application Ser. No. 07/776,816, filed Oct. 15, 1991, the disclosure of which is incorporated by reference herein.

WORKING EXAMPLES

Abbreviations Used in Working Examples

PLC=poly(DL-lactide-co-caprolactone)
DEM=diethyl malonate
PEG=polyethylene glycol
$\epsilon$-CAP=$\epsilon$-caprolactone
NMP=N-methyl-2-pyrrolidone
Apro=Aprotinin
Gz=guaiazulene
EL=ethyl lactate
DMSO=dimethyl sulfoxide
rt-PA=recombinantly produced tissue plasminogen activator
Untreated Control=Surgery was performed, no formulation applied to the tissue defect

EXAMPLE 1

Preparation of Poly(DL)L-lactide-co-caprolactone)

A preferred thermoplastic polymer for use with the invention is poly(DL-lactide-co-caprolactone). Poly(DL-lactide-co-caprolactone) may be synthesized via copolymerization of DL-lactide and $\epsilon$-caprolactone with a multifunctional polyol initiator and a catalyst.

Catalysts useful for the preparation of poly(DL-lactide-co-caprolactone) are preferably basic or neutral transesterification catalysts. Metallic esters of carboxylic acids containing up to 18 carbon atoms, such as formic, acetic, lauric, stearic and benzoic are normally used as such catalysts. Stannous octoate and stannous chloride are preferred catalysts, both for FDA compliance and performance.

If a bifunctional polyester is desired, a bifunctional chain initiator, such as ethylene glycol may be employed. A trifunctional initiator such as trimethylolpropane is used if a trifunctional polymer is desired, etc. The amount of chain initiator used will affect the resultant molecular weight of the polymer or copolymer.

To prepare poly(DL-lactide-co-caprolactone), appropriate amounts of DL-lactide, $\epsilon$-caprolactone and chain initiator are combined in a flask under nitrogen and then heated in an oil bath at a temperature from about 140° to 150° Celsius to melt and mix the monomers. For example, a 75/25 ratio of lactide to caprolactone can be combined with lauryl alcohol as the chain initiator. Copolymerization can be catalyzed by adding 0.03 to 0.05 wt % $SnCl_2$.

The copolymerization reaction is allowed to proceed for about 6 hours. After the monomers have reacted, the mixture is allowed to cool. The cooled copolymer mixture is then dissolved in a solvent such as methylene chloride or acetone. The polymer is precipitated by the addition of water or methanol (the residual monomers remain in solution). The solution containing the residual monomers is poured off and the precipitate containing the polymer is dried to obtain poly(DL-lactide-co-caprolactone).

EXAMPLE 2

Preliminary Screening of Various Polymer Formulations

Various polymer formulations were evaluated for their overall ability to reduce adhesion tenacity and extent. The polymer formulations were capable of being aerosolized when applied at room temperature (approximately 72° F.). Within about 30 seconds after application, the polymer formulation coagulated to form a film with mild to moderate tissue adherence. As used herein "mild to moderate" tissue adherence means that the matrix was not removed by gentle rubbing. Better adherence was obtained when the polymer formulation was applied to dry tissue.

Rabbit Model

The following model was used to evaluate the ability of various polymer formulations to prevent adhesion formation.

Each polymer formulation was administered to a group of six rabbits. All six rabbits in each group received the same uterine horn tissue defect while under general anesthesia.

The following procedure was used to generate the tissue defect. Each rabbit was placed in dorsal recumbency, the abdomen clipped of hair and the surgical site prepared with Betadine® scrub and isopropanol. A mid-line incision was made through the linea alba to provide access to the abdominal cavity.

The two uterine horns were exteriorized and a 1 cm long incision (the "tissue defect") was created longitudinally along the top of the uterine horn, 3 cm distal to the uterine body. Endometrial tissue was everted by securing the incision along proximal tissues with a 4-0 Vicryl® stay suture. The various polymer formulations were sprayed onto the tissue defects using an aerosol applicator with a nitrogen gas propellant. Approximately 0.25 mL–0.50 mL of a polymer formulation was applied to each tissue defect, resulting in a film having a thickness of about 20 $\mu$m–50 $\mu$m.

After the polymer formulation was applied to the tissue defect, the abdominal cavity was closed with a simple continuous suture pattern using 4-0 Vicryl® suture. Torbutrol® (1 cc) was administered for analgesia. Termination was at 14 days, using Beuthanasia-D euthanasia solution.

The following treatments were evaluated.

1. Untreated Control—Surgery was performed, nothing applied to the tissue defect;
2. Gore-Tex™—a piece of Gore-Tex™ film was applied to the defect per manufacturers instructions;
3. Saline—approximately 1 ml of saline was applied to the tissue defect;
4. PLC/NMP/EL—approximately 0.25–50 ml of a polymer formulation containing poly(DL-lactide-co-caprolactone), N-methyl-2-pyrrolidone and ethyl lactate was applied to the tissue defect;
5. PLC/NMP/EL (Saline Spray)—after approximately 0.25–50 ml of the indicated polymer formulation was applied to the tissue defect, approximately 1 ml of saline was sprayed on the formulation using an airbrush; or
6. PLC/NMP/EL (Saline Lavage)—after approximately 0.25–50 ml of the indicated polymer formulation was applied to the tissue defect, approximately 1 ml of saline was poured over the formulation using a syringe with a 18 gauge needle.

Results

Each tissue defect was necropsied, documented, photographed and evaluated for adhesion tenacity, extent and total adhesion score.

For each tissue defect, the adhesion tenacity was evaluated and given a score from 0 to 4. The individual adhesion tenacity score for each defect in an animal were averaged. To obtain a group tenacity score, the average score for each animal was averaged with the scores for the other members of the group.

The maximum score which could be given to an undesirable polymer formulation was 4. Adhesions tenacity was scored as follows:

0=no adhesions
1=filmy adhesions
2=gelatinous adhesions
3=organized adhesions requiring blunt dissection
4=organized adhesions requiring sharp dissection.

Adhesion extent was given a score of either a 0 or 4 for each tissue defect. If no tissue to tissue or intrahorn/interhorn adhesions were present, the score was 0. If adhesions were present, the score was 4. Since the right uterine horn and left uterine horn each received tissue defects, and there was the possibility of intrahorn adhesion formation, the maximum score possible for adhesion extent was 12.

Adhesion tenacity and extent scores for each rabbit in a group were added to obtain a total score for that group. The total score demonstrates a formulation's overall ability to reduce the strength and scope of adhesion formation.

Figure 1:
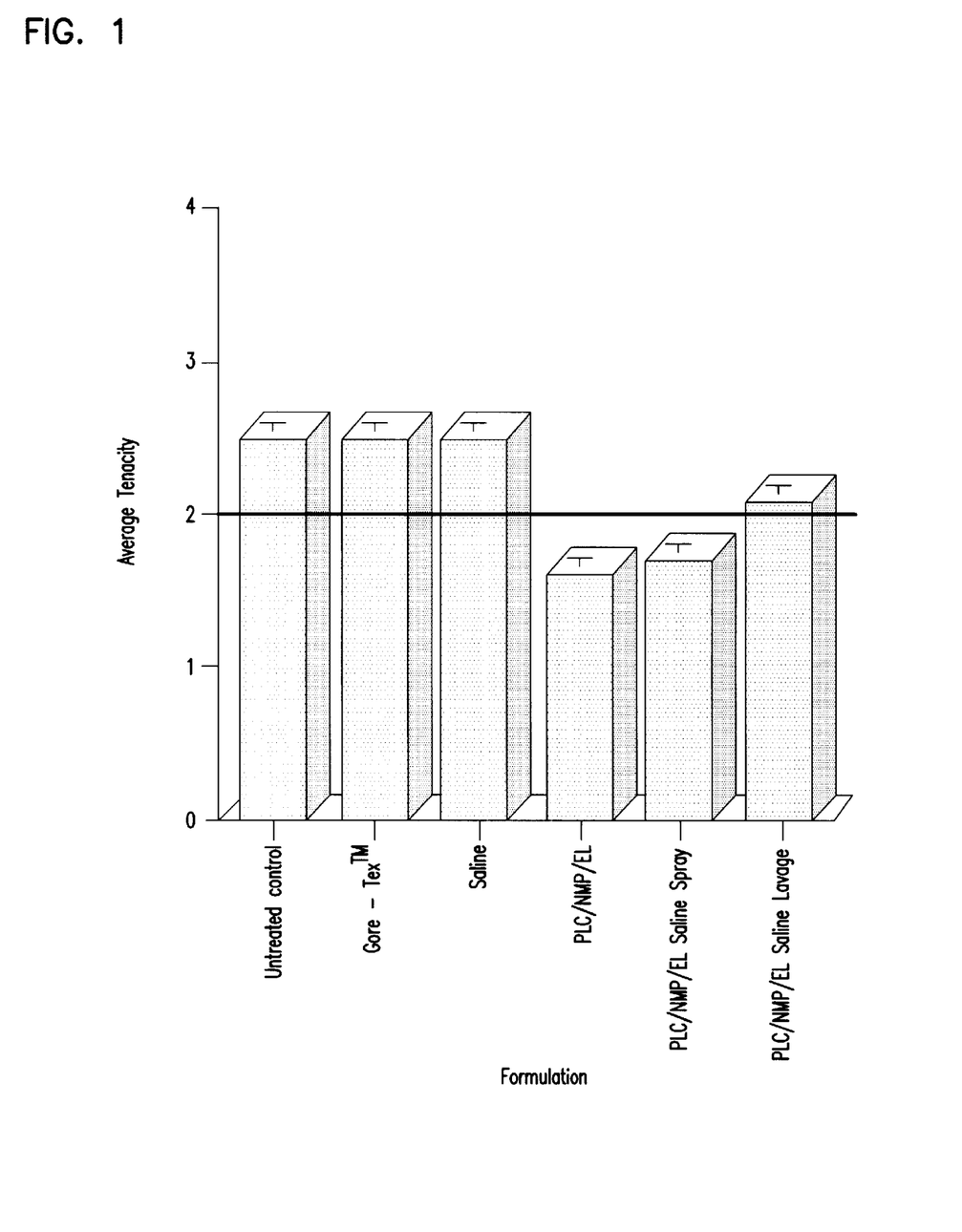
FIG. 1 is a bar graph showing the average tenacity of adhesions for various formulations.
Figure 2:
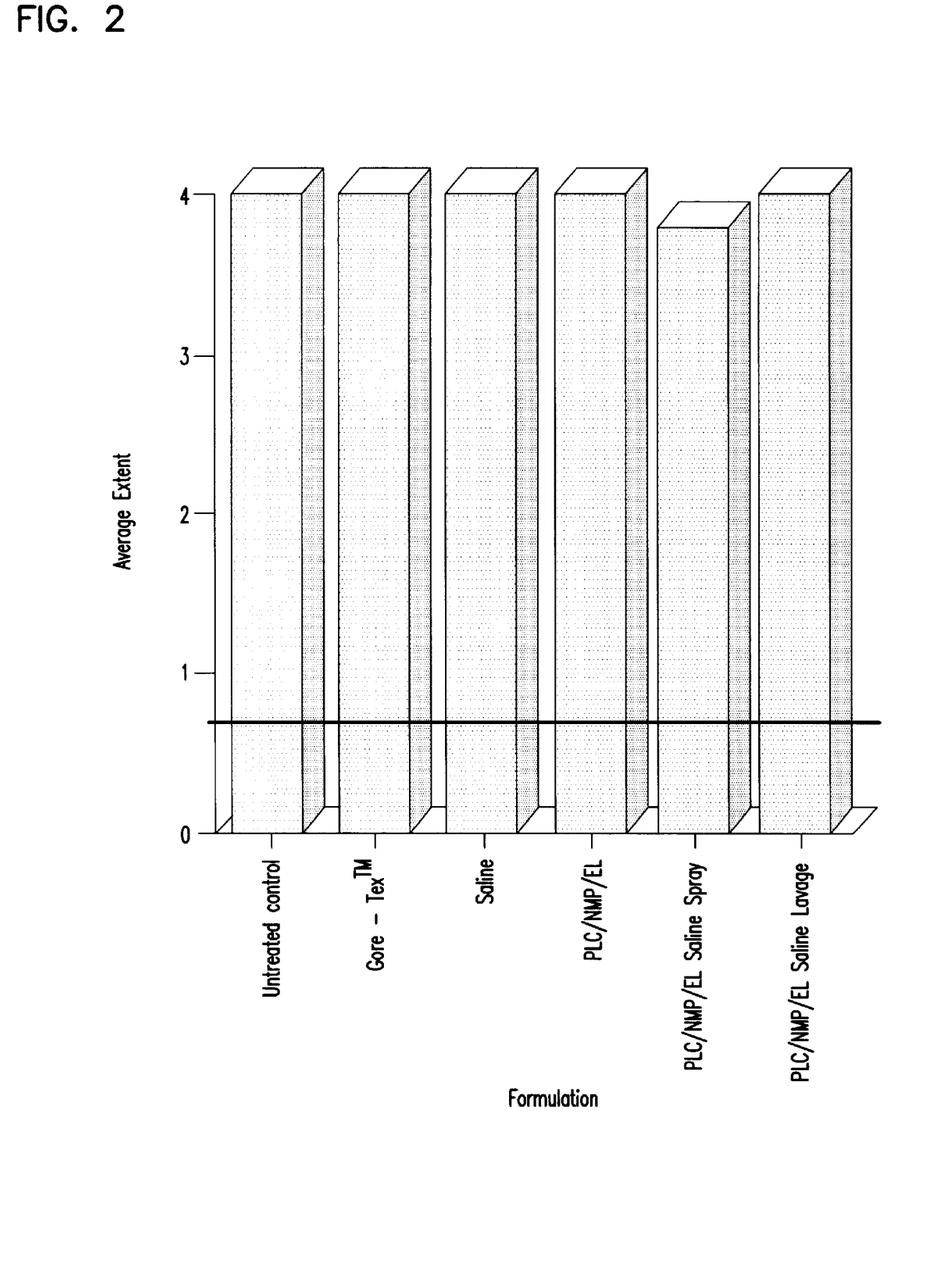
FIG. 2 is a bar graph showing the average extent of adhesion formation for various formulations.
Figure 3:
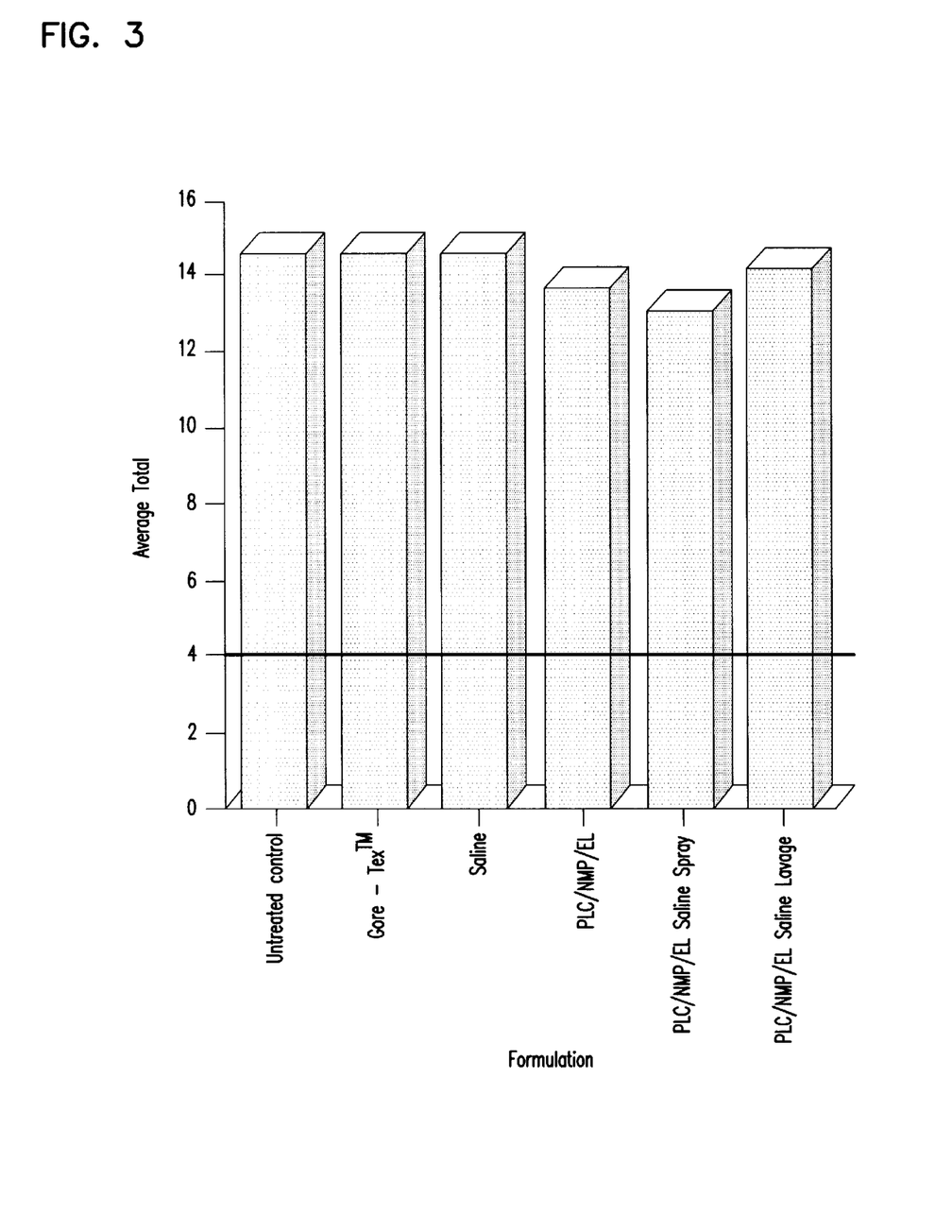
FIG. 3 is a bar graph showing the average total score for various formulations.

The results from this experiment are shown in Table 2-1 and in FIGS. 1–3. Demarcation lines have been added to the Figures to indicate the performance of current therapeutic regimens. The performance of current regimens was taken as the maximum acceptable limit for adhesion tenacity (e.g., 2), extent (e.g., 0.7) and total score (e.g., 4). Any formulation below the demarcation line is considered to be more effective at reducing adhesion formation that currently available products.

TABLE 2-1

Average Adhesion Scores

| Test Article | Average Tenacity | Average Extent | Overall Score |
|---|---|---|---|
| Untreated Control | 2.5 | 12 | 14.5 |
| Gore-Tex ® | 2.5 | 12 | 14.5 |
| Saline | 2.5 | 12 | 14.5 |
| PCL/NMP/BL | 1.6 | 12 | 13.6 |
| PCL/NMP/EL (saline spray) | 1.7 | 12 | 13.0 |
| PCL/NMP/EL (saline lavage) | 2.1 | 12 | 14.1 |

The results in Table 2-1 and FIGS. 1–3 indicate that polymer formulations having NMP as a solvent provide a barrier with some ability to prevent adhesion formation. However, subsequent experiments (see, Table 3-1 and FIG. 4) demonstrate that a number of pharmaceutical additives are required for the NMP formulations to be as effective as polymer formulations having ε-caprolactone as the organic solvent.

EXAMPLE 3

Screening of Additional Polymer Formulations

Figure 4:
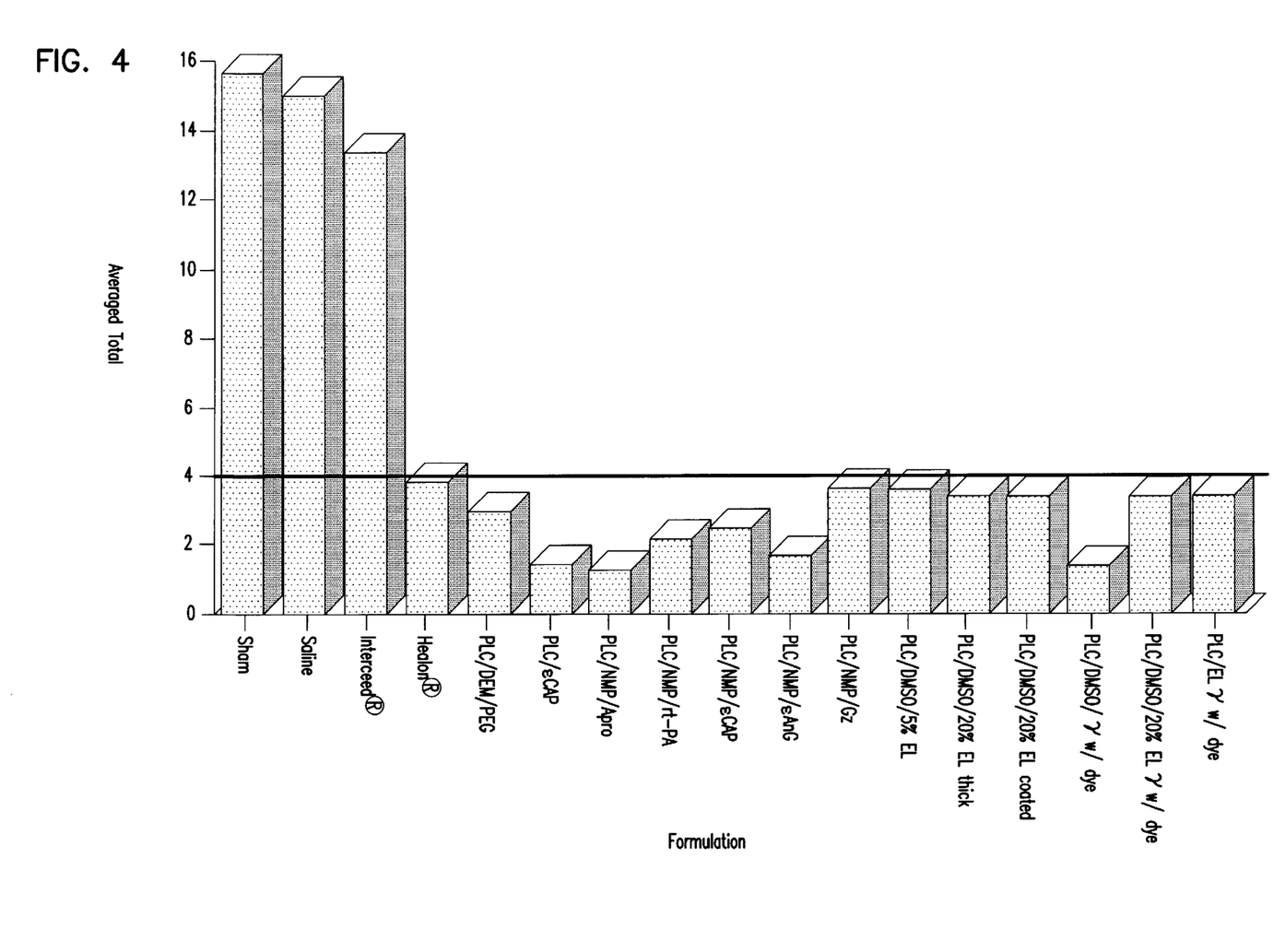
FIG. 4 is a bar graph showing the average total adhesion scores for various formulations.

The same rabbit model described in Example 2 was used to evaluate the ability of additional polymer formulations to prevent adhesion formation. As described in Example 2, each tissue defect was necropsied, documented, photographed and evaluated for adhesion tenacity, extent and total adhesion score. The average total scores for each group are shown in Table 3-1. FIG. 4 corresponds to the data shown in Table 3-1.

A demarcation line has been added to FIG. 4 to indicate the performance of current therapeutic regimens. The performance of current regimens was taken as the maximum acceptable limit for total score (e.g., 4). Thus, any formulation below the demarcation line was considered more effective at reducing adhesion formation than products currently available.

TABLE 3-1

Average Total Scores for Various Formulations

| Formulation | Average Total Score for group |
|---|---|
| Untreated Control | 15.4 |
| Saline | 15.0 |
| Interceed ® | 13.3 |
| Healon ® | 3.8 |
| 12.5% 75/25 PLC (IV 0.74 dL/g)/82.5% DEM/5% PEG | 2.9 |
| 15% 75/25 PLC (IV 0.74 dL/g)/85% ε-CAP | 1.4 |
| 15% 75/25 PLC (IV 0.74 dL/g)/84.9% NMP/0.06% Apro | 1.7 |
| 15% 75/25 PLC (IV 0.74 dL/g)/84.9% NMP/0.1% rt-PA | 2.1 |
| 15% 75/25 PLC (IV 0.74 dL/g)/25% NMP/60% ε-CAP | 2.4 |
| 12.5% 75/25 PLC (IV 0.74 dL/g)/82.5% NMP/5% εAnC | 1.6 |
| 12.5% 75/25 PLC (IV 0.74 dL/g)/82.5% NMP/5% Gz | 3.6 |
| 12.5% 75/25 PLC (IV 0.74 dL/g)/82.5% DMSO/5% EL | 3.6 |
| 5% 75/25 PLC (IV 0.74 dL/g)/75% DMSO/20% EL applied as a thick film | 3.4 |
| 5% 75/25 PLC (IV 0.74 dL/g)/75% DMSO/20% EL entire area coated | 3.4 |
| 15% 75/25 PLC (IV 0.74 dL/g)85% DMSO irradiated with dye added | 3.4 |
| 12% 75/25 PLC (IV 0.74 dL/g)/68% DMSO/20% EL irradiated with dye added | 3.4 |

TABLE 3-1-continued

Average Total Scores for Various Formulations

| Formulation | Average Total Score for group |
|---|---|
| 5% 75/25 PLC (IV 0.74 dL/g)/95% EL non-irradiated with dye added | 3.4 |

The following polymer formulations resulted in an average total score less than or equal to Healon®, a current therapeutic regimen. Therefore, these formulations are considered to perform better than the currently available therapeutic regimen.
1. 12.5% 75/25 PLC (IV 0.74 dL/g)/82.5% DEM/5% PEG
2. 15% 75/25 PLC (IV 0.74 dL/g)/85% ε-CAP
3. 15% 75/25 PLC (IV 0.74 dL/g)/84.9% NMP/0.06% Aprotinin
4. 15% 75/25 PLC (IV 0.74 dL/g)/84.9% NMP/0.1% rt-PA
5. 15% 75/25 PLC (IV 0.74 dL/g)/25% NMP/60% ε-CAP
6. 12.5% 75/25 PLC (IV 0.74 dL/g)/82.5% NMP/5% εAnC
7. 12.5% 75/25 PLC (IV 0.74 dL/g)/82.5% NMP/5% Gz
8. 12.5% 75/25 PLC (IV 0.74 dL/g)/82.5% DMSO/5% EL
9. 5% 75/25 PLC (IV 0.74 dL/g)/75% DMSO/20% EL (as a thick film or entire area coated)
10. 15% 75/25 PLC (IV 0.74 dL/g)/85% DMSO (gamma irradiated with dye)
11. 12% 75/25 PLC (IV 0.74 dL/g)/68% DMSO/20% EL (gamma irradiated with dye)
12. 5% 75/25 PLC (IV 0.74 dL/g)/95% EL (non-irradiated with dye)

The following polymer formulations are most preferred.
1. 15% 75/25 PLC (IV 0.74 dL/g)/85% ε-CAP
2. 15% 75/25 PLC (IV 0.74 dL/g)/84.9% NMP/0.06% Apro
3. 15% 75/25 PLC (IV 0.74 dL/g)/84.9% NMP/0.1% rt-PA
4. 15% 75/25 PLC (IV 0.74 dL/g)/25% NMP/60% ε-CAP
5. 12.5% 75/25 PLC (IV 0.74 dL/g)/82.5% NMP/5% εAnC
6. 15% 75/25 PLC (IV 0.74 dL/g)/85% DMSO (gamma irradiated with dye)

The results from this experiment indicate that polymer formulations having ε-caprolactone as the organic solvent, or NMP as the organic solvent in combination with a pharmaceutical additive, provide a superior reduction in adhesion formation when compared to currently available treatments. Based on the results from this screening study, three formulations were selected to be tested in a more standard uterine horn abrasion model. (See, Examples 4 & 5)

EXAMPLE 4

Formulation Preparation

Three polymer formulations were prepared for further evaluation using a standard rabbit uterine horn model.
A. 19.96% 64/36 PLC (0.74 dL/g)/79.97% NMP/0.03% εAnC
B. 15% 64/36 PLC (0.74 dL/g)/85% εCAP
C. 19.99% 64/36 PLC (0.74 dL/g)/79.97% εCAP/0.06% Aprotinin To prepare these formulations, dry poly(DL-lactide-co-caprolactone) (PLC) was weighed into glass vials. Appropriate amounts of solvent, either N-methyl-2-pyrrolidone (NMP) or ε-caprolactone (ε-CAP), were added to the glass vials containing the polymer to form a mixture having a polymer concentration of about 20%. The glass vials containing the samples were placed on an environmental shaker at room temperature (about 25° C.) until the polymer dissolved.

Formulations A and C were diluted from a concentration of about 20 wt-% polymer to a concentration of 15 wt-% polymer to enhance sprayability of the polymer formulation. Therefore, the formulations, as used in Examples 4 and 5 contained the following:
A. 15% 64/36 PLC (IV 0.74 dL/g)/85% NMP with 0.03% εAnC
B. 15% 64/36 PLC (IV 0.74 dL/g)/85% ε-CAP
C. 15% 64/36 PLC (IV 0.74 dL/g)/85% ε-CAP with 0.06% Aprotinin Formulation A, containing NMP as a solvent, required only 24 hours to dissolve the polymer. Formulations B and C, containing ε-CAP as a solvent, required four to five days to dissolve the polymer, along with occasional physical mixing with a glass stir rod.

Once the polymer was dissolved, the formulations were sterile filtered, under a $N_2$ pressure of 60 psi, using a TefSep, Teflon, laminated 0.22 micron filter. Approximately 10 to 15 minutes was required to filter 16 grams of each formulation.

ε-Amino-n-caproic acid (0.03%) and aprotinin (0.06%) were added to formulations A and C, respectively. The formulations were mixed using the "syringe system", wherein the drug was loaded in a first syringe and the polymer/solvent mixture was loaded into a second syringe. The two syringes were coupled together and the contents were physically mixed back and forth. Neither drug (Aprotinin or ε-amino-n-caproic acid) dissolved in the polymer formulation. Therefore, samples were mixed until a homogeneous suspension was obtained. After mixing, 0.6 mL of each formulation was transferred to separate sterile 1 mL vials and capped.

The diluted formulations (containing about 15% polymer) were too viscous to obtain a continuous spray when administered by aerosol due to the temperature of the operating room (60–65° F.). Therefore, each formulation was applied by aspirating the formulation from the vial into a syringe with a 20 gauge needle. The formulation was then dripped onto the tissue defect.

It was observed that the formulation having NMP as a solvent coagulated quickly and adhered to itself, gloves and instruments. The formulations having ε-CAP as a solvent did not have these problems.

EXAMPLE 5

Adhesion Study

The three "diluted" polymer formulations made in Example 4 were evaluated to determine their efficacy in preventing formation of adhesions in a standard rabbit uterine horn model.

Protocol

Forty eight female New Zealand White Rabbits (*Oryctolagus cuniculus*), weighing between 2.4 and 3.0 kg, were obtained from Myrtle Farms, Thompson Station, Tenn. These rabbits were used to evaluate the effect of various treatments on the formation of adhesions.

Animals were randomized, with seven animals in each of the six groups, to receive one of the following treatments:
A. 15% 64/36 PLC (IV 0.74 dL/g)/85% NMP with 0.03% ε-AnC;
B. 15% 64/36 PLC (IV 0.74 dL/g)/85% ε-CAP;
C. 15% 64/36 PLC (IV 0.74 dL/g)/85% ε-CAP with 0.06% Apro;

D. Seprafilm™ Bioresorbable Membrane (Genzyme Corp, Cambridge Mass.);

E. Interceed™ (TC7) Absorbable Adhesion Barrier (Ethicon, Inc. Somerville, N.J.); or F. Untreated Control.

Rabbit Uterine Horn Abrasion Model

The rabbit uterine horn model was conducted essentially as described by Wiseman et al., *J. Reprod. Med.*, 37:766–770 (1992).

Animals were weighed on the day of surgery. Anesthesia was induced and maintained by inhalation of isoflurane (3.5 and 5% concentrations, respectively). Depilation of the surgical site was accomplished with an electric animal clipper. The area was vacuumed to remove hair clippings and debris, and then rinsed with alcohol. The entire area was painted with an aqueous iodophor solution (iodine scrub) of 1% available iodine. The area was then swabbed with 70% isopropyl alcohol solution and reswabbed with iodine preparation solution.

Procedures were performed in a sterile manner in a room reserved for aseptic survival surgery. Sterile towels, drapes and instruments were used. The anesthetized and surgically prepared rabbit was delivered to the operating table and restrained, via the limbs, in a recumbent position. The surgical site was cleansed again with 70% isopropyl alcohol. A sterile incise drape was applied to the prepared area.

A midline incision was made through the skin and the abdominal wall. Both uterine horns were located and exteriorized. Using a French Catheter Scale, the diameter of each uterine horn was measured and recorded. Only those rabbits with uterine horns measuring size 8–16, inclusive, on the French scale were entered into this protocol.

Using a number 10 scalpel blade, 5 cm lengths of each uterine horn, approximately 1 cm from the uterine bifurcation were scraped, 40 times per side, until punctuate bleeding. Hemostasis was achieved by tamponade.

The surgeon was made aware of the random assignment after completion of the abrasion procedures and attainment of hemostasis. A 2.5×3.25 cm piece of Interceed™ Barrier was placed over each horn designated to receive it, and applied per manufacturer instructions. For animals designated to receive Seprafilm™, a piece approximately 4×6 cm was applied to each uterine horn per manufacturer's instructions. Although it was intended that the polymer formulations were to have been delivered via airbrush, due to cold temperatures in the operating room (60°–65° F.), the three polymer formulations were not effectively administered using an aerosol spray. Therefore, 0.45 to 0.9 ml of polymer formulation was dripped over the horns using a 20 gauge needle and syringe.

Uterine horns were then replaced into the pelvis and the abdominal incision closed using a continuous Vicryl™ 4-0 suture. Fascia was closed loosely with 4-0 Vicryl™ and the skin closed with undyed 4-0 Vicryl (cutting needle) using a subcuticular suturing method.

A total of five doses of Butorphanol tartrate (0.1–0.2 mg/kg) was given by subcutaneous injection, one immediately after surgery and thereafter twice a day for two days. The incision line was inspected daily for signs of dehiscence and bleeding.

Approximately sixteen (16±1) days after surgery, animals were euthanized by intravenous injection of sodium pentobarbital (120 mg/ml; 1 ml/kg). Body weights of the animals were recorded. The abdomen was opened and the surgical site inspected. Adhesions were graded, as described below, by a blinded observer.

Average Extent

The average extent was determined by measuring the total length (cm) of each uterine horn involved with adhesions. For each animal, the average extent of adhesions was calculated for both uterine horns. The score for both uterine horns was then averaged and used in calculating the mean extent of adhesions for the group.

Incidence

The incidence of adhesions in each animal was determined by counting the number of horns with adhesions for each group of seven rabbits (14 uterine horns total). The incidence is shown as number of uterine horns free of adhesions in a group over the total number of uterine horns in that group.

Uterine Horn Results

The results are shown in Table 5-1. Extensive adhesions formed in all but three control uterine horns. Although the average extent was a little low, the extent of adhesions found in this group was within the normal range.

Interceed™ Barrier reduced adhesion formation, although only slightly. Large material remnants were found in these animals. The poor performance of Interceed™ barrier in this study is possibly related to the presence of the material remnants.

Reduction in extent and incidence of adhesions, although not statistically significant was noted in animals treated with Seprafilm™. Inspection of the results show a broad range of responses from complete prevention of adhesions in two animals, to maximal adhesion formation in two animals. The highly variable performance (2.50±0.799 cm) of Seprafilm™ may have been related to its poor handling characteristics. Additionally, upon application, Seprafilm™ cracked easily, thus removing the protective effect of the barrier.

Formulation B reduced both the incidence (11/14 horns with adhesions) and extent (1.79±0.644 cm) of adhesions, compared with the control (13/14 horns with adhesions, 3.21±0.623 cm extent). Formulation A appeared to enhance adhesion formation, while a small reduction in adhesion formation (2.54±0.751) was noted with formulation C.

TABLE 5-1

Effect of polymer formulations on adhesion formation

| Group | Extent[1] | Incidence[2] |
|---|---|---|
| A (Formulation A) | 4.11 (0.429) | 0/14 |
| B (Formulation B) | 1.79 (0.644) | 3/14 |
| C (Formulation C) | 2.54 (0.751) | 1/12 |
| D (Seprafilm ™) | 2.50 (0.779) | 4/14 |
| E (Interceed ™) | 2.83 (0.738) | 0/12 |
| F (Control) | 3.21 (0.623) | 1/14 |

[1]Length of uterine horn with adhesions; cm (± Standard Error of the Mean)
[2]Number of uterine horns free of adhesions/total Conclusion Formulation B, containing poly(DL-lactide-co-caprolactone) and ε-caprolactone, effected a reduction in both the incidence and extent of adhesions. The performance of this formulation was equivalent to that observed historically with Interceed™ Barrier in this model. (Wiseman et al, "Improving the Efficacy of Interceed™ Barrier in the Presence of Blood Using Thrombin, Heparin, or a Blood Insensitive Barrier, Modified Interceed™ (n TC7)", In: *Gynecologic Surgery and Adhesion Prevention*, eds. Diamond et al., Wiley-Liss, New York, pp. 205–212 (1993)).

A small reduction in adhesion formation was noted with Formulation C (poly(DL-lactide-co-caprolactone dissolved in ε-caprolactone with 0.06% aprotinin).

Formulation A, (poly(DL-lactide-co-caprolactone dissolved in N-methyl-2-pyrrolidone with 0.03% ε-amino-n-caproic acid) appeared to enhance adhesion formation. The application of more polymer formulation by dripping versus spraying, demonstrated the intrinsic characteristics and flexibility of the polymer formulations and their adaptability to various scenarios.

The results indicate that the polymer formulations having caprolactone as a solvent (with or without pharmacological agent) provide better adhesion prevention than the Untreated Control, Saline or currently available treatments.

The invention has been described with reference to various specific and preferred embodiments and techniques. However, it should be understood that many variations and modifications may be made while remaining within the spirit and scope of the invention.

What is claimed is:

1. A polymer formulation suitable for use in preventing adhesions comprising:
   (a) ε-caprolactone;
   (b) a pharmaceutically acceptable biodegradable thermoplastic polymer that is substantially insoluble in an aqueous or body fluid and soluble in ε-caprolactone; and
   (c) a biologically active agent capable of being dissolved, dispersed or suspended in ε-caprolactone wherein the thermoplastic polymer is dissolved in the ε-caprolactone and the biologically active agent is dissolved, dispersed or suspended in the ε-caprolactone.

2. The polymer formulation of claim 1, wherein the biologically active agent is an anti-inflammatory agent.

3. The polymer formulation of claim 2, wherein the anti-inflammatory agent is a corticosteroid selected from the group consisting of hydrocortisone, and prednisone.

4. The polymer formulation of claim 2, wherein the anti-inflammatory agent is a nonsteroidal agent selected from the group consisting of flurbiprofen or ibuprofen.

5. The polymer formulation of claim 1, wherein the biologically active agent prevents the deposition of fibrin or enhances fibrinolysis.

6. The polymer formulation of claim 5, wherein the biologically active agent is selected from the group consisting of heparin, sodium citrate, pentoxifylline, tissue plasminogen activator (rt-PA), urokinase, streptokinase, aprotinin (Aprot), and ε-amino-n-caproic acid (εAnC).

7. The polymer formulation of claim 1, further comprising a rate release modification agent.

* * * * *